United States Patent [19]

Beraha

[11] Patent Number: 4,600,014
[45] Date of Patent: Jul. 15, 1986

[54] TRANSRECTAL PROSTATE BIOPSY DEVICE AND METHOD

[76] Inventor: Dan Beraha, 912 Woodbriar Ct., Fort Walton Beach, Fla. 32548

[21] Appl. No.: 579,158

[22] Filed: Feb. 10, 1984

[51] Int. Cl.⁴ ............................................. A61B 10/00
[52] U.S. Cl. ..................................... 128/754; 128/310
[58] Field of Search ............... 128/749, 751, 752, 753, 128/754, 303.15, 310

[56] References Cited

U.S. PATENT DOCUMENTS

| | | | |
|---|---|---|---|
| 2,004,559 | 6/1935 | Wappler et al. | 128/303.15 |
| 3,477,423 | 11/1969 | Griffith | 128/754 |
| 3,587,560 | 6/1971 | Glassman | 128/753 |
| 3,995,619 | 12/1976 | Glatzer | 128/749 |
| 4,243,048 | 1/1981 | Griffin | 128/751 |
| 4,249,541 | 2/1981 | Pratt | 128/753 |
| 4,362,160 | 12/1982 | Hiltebrandt | 128/303.15 |
| 4,396,021 | 8/1983 | Baumgartner | 128/753 |

FOREIGN PATENT DOCUMENTS

| | | | |
|---|---|---|---|
| 10321 | 4/1980 | European Pat. Off. | 128/754 |
| 249551 | 12/1969 | U.S.S.R. | 128/754 |
| 400319 | 2/1974 | U.S.S.R. | 128/753 |
| 707576 | 1/1980 | U.S.S.R. | 128/754 |

*Primary Examiner*—David Shay
*Attorney, Agent, or Firm*—Macdonald J. Wiggins

[57] ABSTRACT

An improved biopsy needle suitable for obtaining a core sample from a prostate gland. A handle which may be held in the palm of the physician's hand is provided with a forward extending guide tube. A cannula with a sharpened distal end is slidably disposed within the guide tube and is movable by a thumb tab from a retracted position within the guide tube to an extended position in which the cutting edge extends from the guide tube. A sampling stylet having a sharpened distal end and a sample-collecting slot therein is telescopically disposed within the cannula and projects from the rear of the handle. A knob at the proximal end of the stylet permits movement from a retracted position in which the pointed tip of the stylet projects slightly from the distal end of the guide tube to an extended position in which the pointed distal end extends from the guide tube distal end. The physician holding the handle in the palm of his hand places his index finger at the distal end of the guide tube and guides the distal end to a selected point on the prostate gland transrectally. Upon locating the desired point, the hand holds the instrument steady while the other hand pushes the stylet forward into the tissue, pushes the cannula forward to sever tissue within the sampling slot, and the device is then withdrawn with the desired sample.

9 Claims, 7 Drawing Figures

TRANSRECTAL PROSTATE BIOPSY DEVICE AND METHOD

BACKGROUND OF THE INVENTION

1. Field of the Invention

The present invention relates to a prostatic biopsy needle and more particularly to a medical instrument that can provide a reasonable core of prostatic tissue through a transrectal or transperineal route.

2. Description of the Prior Art

In the diagnosis of malignancies of the prostate gland, it is known to utilize cytologic studies based on a fine needle aspiration biopsy. For example, a device for this purpose is disclosed in U.S. Pat. No. 3,595,217 to Rheinfrank. A hollow biopsy needle is passed through a guide tube attached to the operator's finger which is placed on the prostate gland. The needle penetrates the gland and a syringe attached to the needle withdraws a tissue sample. Unfortunately, the use of an aspirating needle to obtain samples from the prostatic tissue has not, in general, produced satisfactory diagnostic material and this approach has been largely abondoned in the United States.

Consequently, a preferred approach is to obtain a core sample. Many physicians utilize a biopsy needle available from Travenol Laboratories, Inc., of Deerfield, Ill. The Travenol TRU-CUT ® biopsy needle comprises a hollow tubular cutting cannula having a sharpened distal end attached to a plastic handle. A coaxial solid stylet telescopes within the cannula and is attached to a knob at its proximal end. The distal end of the stylet is sharpened and includes a transverse slot or specimen notch adjacent to the sharpened end.

To obtain a prostatic sample using the Travenol needle, the physician positions the stylet to project slightly from the cannula. The index finger of one hand is placed along the cannula with the tip in contact with the stylet distal end and the handle is held in the palm. Approaching the prostate gland transrectally, the gland is explored with the finger tip to locate a nodule or suspicious area. After locating a point for a sample, the needle is eased forward into the nodule. Once in place, the stylet is plunged to the desired depth.

The physician then must then remove his hand and finger, grasp the stylet knob in one hand, and push the cannula handle forward with the other hand. Theoretically, the cutting end moves along the stylet and severs a sample of tissue projecting into the transverse slot in the tip of the stylet. The entire needle is then withdrawn from the gland and the sample removed from the stylet.

In practice, the manipulation of the cannula during this latter step is quite difficult since the tip of the stylet is embedded in the soft and pliable prostatic tissue several inches from the handle. The stylet knob gives very little steady support to the needle assembly and the stylet tip, due to its smaller diameter, penetrates the tissue somewhat easier than the tubular cannula cutting edge. On occasions, when attempting to push the cannula into the tissue, the entire needle moves forward, puncturing the bladder or urethra. It is also common to attempt to move the cannula forward only to have the stylet back out of the tissue. When this occurs, the physician must remove the needle, reposition the stylet, and try again.

Since the procedure involves puncturing of the colon wall, each attempt increases the risk of infection. Most physicians limit such attempts to two or three passes. Even with a successful insertion of the cannula, the instability of the Travenol needle often results in a limiting core sample.

Thus, there is a long-felt and unfilled need for a transrectal biopsy needle which can be guided to the required point of the prostate gland by the physician's finger, a sampling stylet inserted, and a cutting cannula plunged forward without removal of the finger.

SUMMARY OF THE INVENTION

My invention is an improvement on the Travenol TRU-CUT ® biopsy needle. A plastic handle in the form of an elongated rectangular block is provided having a hollow guide tube extending from its forward end with the proximal end of the tube anchored in the handle. The distal end of the guide tube is smooth and rounded to prevent abrasion of tissue. A hollow cannula is slidably disposed in telescoping relationship to the guide tube. The proximal end of the cannula is attached to a thumb tab disposed in a slot in the handle. When the thumb tab is fully retracted, the distal end of the cannula is sheathed within the distal end of the guide tube. At the most forward position of the cannula, its distal end extends a preselected distance from the distal end of the guide tube. This distance may be on the order of 2 to 3 cm. The distal end of the cannula is cut at an angle to form a cutting edge thereof.

A sampling stylet, which may be solid, is inserted through an opening in the rear end of the handle into the cannula. A push knob is attached to the proximal end of the stylet. The knob includes a detent attached to the handle to hold the stylet in a retracted position. In such position, the distal end of the stylet which is sharpened projects about 1 cm beyond the distal end of the guide tube. The knob may be pushed forward until it stops against the rear end of the handle causing the distal end of the stylet to project 2 to 4 cm beyond the guide tube. The distal end of the stylet includes a transverse slot or notch for capturing a tissue sample.

As may now be recognized, I provide a core sampling biopsy needle that includes a handle having a fixed guide tube. With the cannula and the stylet fully retracted, the physician uses the tip of the index finger to guide the tip of the guide tube and the slightly projecting stylet to a point on the prostate gland from which a tissue specimen is required while holding the handle in the palm of the hand. Once the device is in place, the hand and finger are held stationary for the remainder of the procedure.

The physician uses his other hand to push the stylet knob forward, penetrating the gland with the stylet. Next, he plunges the cannula forward into the gland, slicing a core of tissue captured within the transverse slot in the distal end of the stylet. At this point, the physician removes the device from the gland with the sample. Thus, the procedure is quickly and efficiently accomplished with minimum risk to the patient.

As may now be recognized, my improved biopsy needle eliminates the major problems encountered using the Travenol-type needle. The handle and guide tube permit the physician to maintain one finger in contact with the gland and to hold the handle perfectly steady in the palm of the hand. The stylet cannot back out of the tissue and the larger diameter of the guide tube ensures that the entire needle does not move forward. Thus, the danger of puncturing the bladder or urethra is eliminated.

Therefore, it is a principal object of my invention to provide an improved transrectal biopsy needle for producing a core tissue sample quickly and accurately.

It is another object of my invention to provide a biopsy needle that can be guided to a desired location within the patient's body by means of a finger which is maintained in place during the remainder of the procedure.

It is still another object of my invention to provide a biopsy needle which may be guided to a desired location by the physician, using one hand, and be held steady by that hand while the other hand is used to collect a tissue sample.

It is a further object of my invention to provide a biopsy needle having an external guide tube, a sharpened cutting cannula telescoping within the guide tube, and a stylet having a tissue-collecting slot in the distal end thereof telescoped within the cannula in which the guide tube is located by the physician at a desired point and remains stationary at that point during the remainder of the tissue-collecting procedure.

It is yet a further object of my invention to provide a biopsy needle having a handle held in the palm of the physician's hand with the guide tube attached thereto and extending therefrom and in which the handle includes means for advancing the stylet and the cannula.

These and other objects and advantages of the invention will become apparent from the following detailed description when read in conjunction with the drawings.

BRIEF DESCRIPTION OF THE DRAWINGS

FIGS. 4, 5, and 6 illustrate the sequence of operation of the tissue sample-collecting portion of my invention in which:

FIG. 4 shows the guide tube having the stylet and cannula retracted with the tip of the stylet inserted into tissue; and FIG. 5 shows the cannula retracted and the stylet plunged forward to a depth suitable for collecting a sample of the tissue;

FIG. 6 shows the cutting cannula plunged forward severing a sample of the tissue in a slot in the stylet tip.

DETAILED DESCRIPTION OF THE PREFERRED EMBODIMENT

Figure 1:
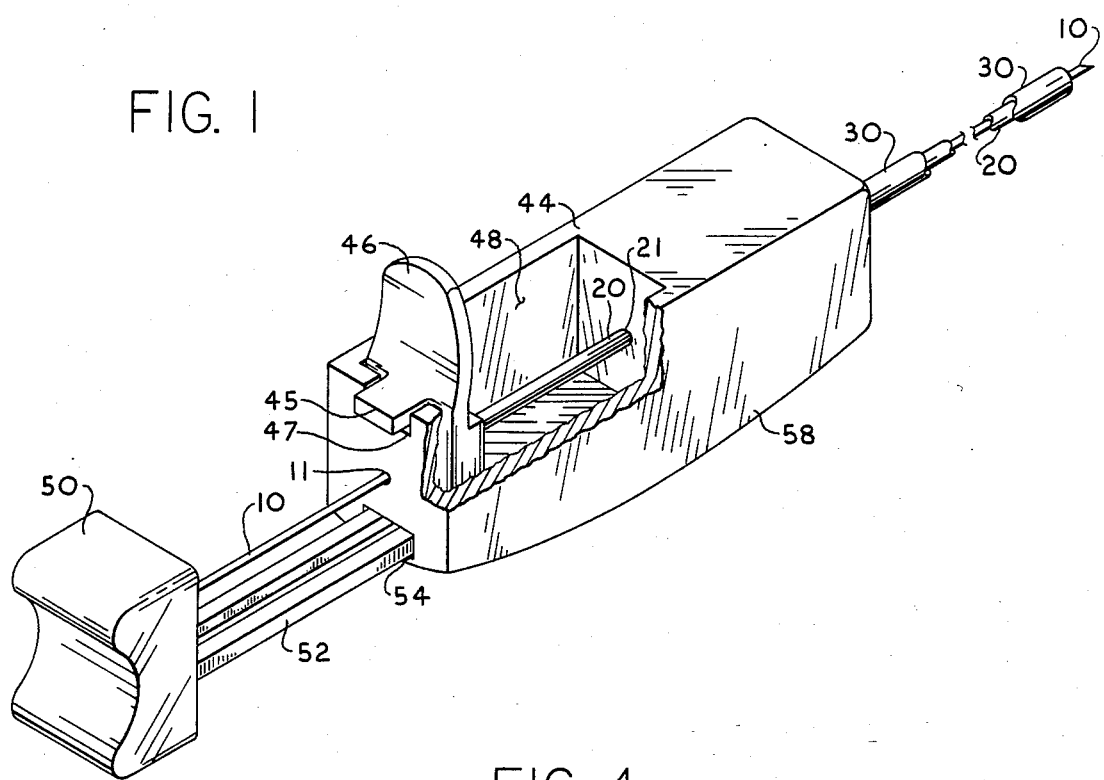
FIG. 1 is a perspective view of one embodiment of my invention having cut away parts to illustrate the construction thereof.
Figure 2:
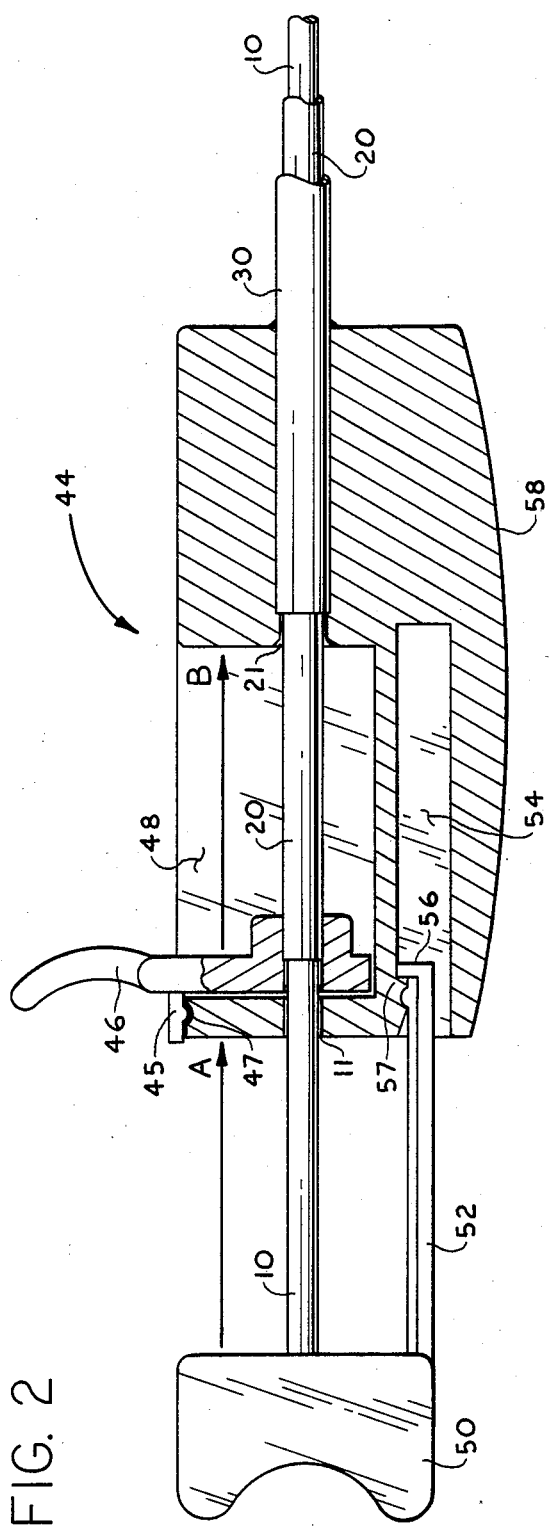
FIG. 2 is a cross-sectional view of the handle portion of the biopsy needle of FIG. 1.
Figure 3:
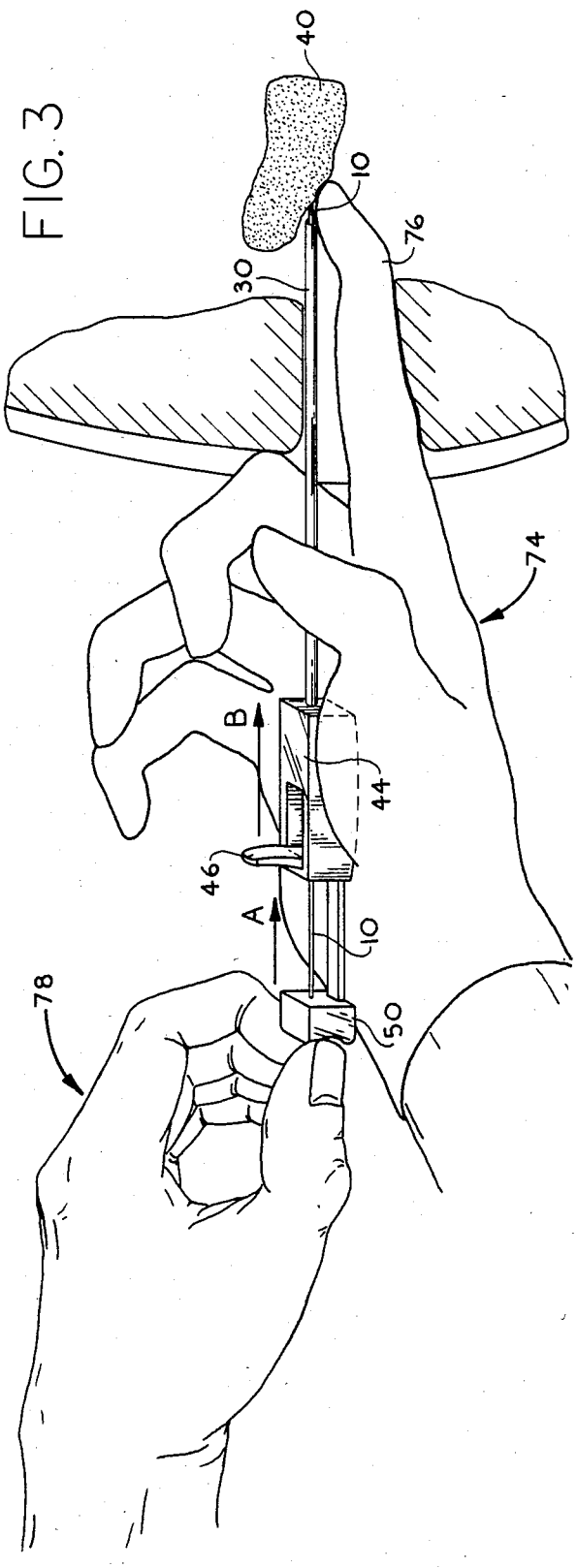
FIG. 3 is a view showing the use of my invention in which the physician has guided the guide tube and stylet point to a desired point on a prostate gland.

Referring to FIGS. 1 and 2, the various elements of my improved transrectal biopsy needle may be noted. Although the description herein below may make reference to certain materials and constructions, it will be obvious to those of skill in the art to adapt other materials and arrangements of the elements, and the illustrations are for exemplary purposes only. I prefer to utilize a handle 44 formed from plastic, such as polystyrene, and designed for the needle to be disposable after use.

Handle 44 preferably includes a curved bottom portion 58 which will fit comfortably in the physician's palm. A recess or slot 48 is provided in the rear portion of handle 44 as well as a slot 54 adjacent the bottom surface 58. A guide tube 30 is disposed in the forward end of handle 44 as best seen in FIG. 2 and is cemented or otherwise anchored therein. Guide tube 30 may be of any suitable material, such as stainless steel, and may have a projecting length on the order of 11 to 16 cm and an outside diameter of about 2 mm. Slidably disposed within guide tube 30 is cutting cannula 20 having a diameter of about 1.5 mm and an overall length of about 15 to 20 cm. As may be noted from FIG. 2, the proximal end of cannula 20 is provided with a thumb tab 46 attached thereto. Thumb tab 46 is configured to fit recess 48 and to be able to slide from the rear position shown in FIG. 2 to a forward position as indicated by arrow B. The amount of movement will depend upon the size of sample desired; however, a movement of about 2 cm is typical. An opening 21 in the forward end of body 44 includes clearance for cannula 20 to permit it to slide easily within guide tube 30.

A catch tab 45 is attached to the rear of thumb tab 46 to engage a depression 47 in the rear end wall of body 44. When cannula 20 is fully retracted, as shown in FIG. 2, catch tab 45 and recess 47 will maintain such position until the physician desires to move cannula 20 forward.

A stylet 10, which may have a length of about 19 to 24 cm and a diameter of about 1 mm, is telescopically disposed within cannula 20 and extends through opening 11 in the rear wall end of body 44 and thumb tab 46. A push knob 50 is attached to the proximal end of stylet 10 and is movable forward to contact the rear wall of body 44 as indicated by arrow A in FIG. 2. A movement forward of about 2.5 cm is suitable. A stopbar 52 provided with a catch portion 56 is connected to push knob 50. Stopbar 52 is shown in FIG. 2 in the full rearward position in which catch 56 has engaged tab 57 in recess 54. Preferably, knob 50 and stopbar 52 are formed from plastic which has sufficient flexibility to cause catch 56 to disengage when a slight forward pressure is placed on push knob 50. With both stylet 10 and cannula 20 in their fully retracted positions, the distal end of cannula 20 does not extend beyond the distal end of guide tube 30 while the tip of stylet 10 extends slightly beyond the distal end of guide tube 30.

Figure 4:
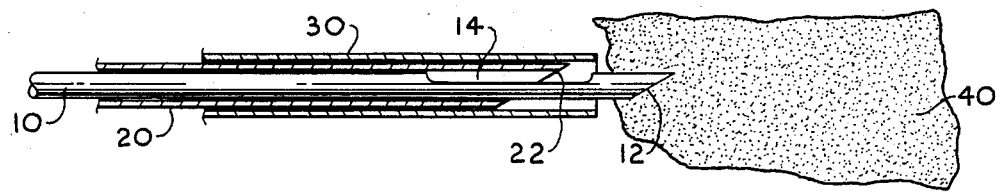
Figure 5:
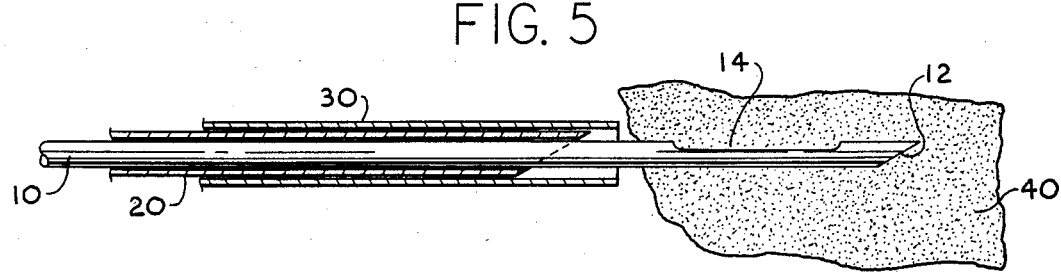
Figure 6:
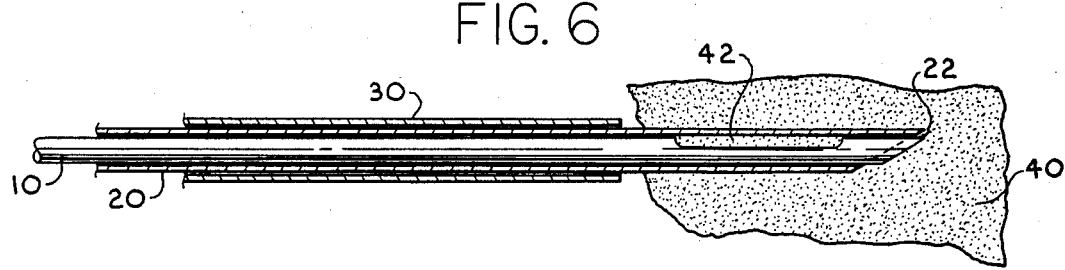

Turning now to FIGS. 3 through 6, additional features of my invention and the method of use will be described. In the particular application of my invention for producing core tissue samples from a prostate gland, the physician places the handle 44 in the palm of the right hand with thumb tab 46 projecting outward. The tip of the index finger 76 is placed at the distal end of guide tube 30 which is in the condition illustrated by the cross-sectional view of FIG. 4 with stylet 10 and cannula 20 fully retracted. The physician permits the tip of stylet 10 having a sharpened portion 12 to be forced against the fingertip. Using the right hand only, he inserts the index finger 76 and guide tube 30 into the patient's rectum and contacts the prostate gland 40 with the finger tip. The physician may then explore the surface of the gland to find a nodule or other suspicious portion thereof. At that point, he may force the sharpened tip 12 of stylet 10 into the nodule as indicated in FIG. 4. Next, the physician, using the left hand 78, pushes push knob 50 forward as indicated by arrow A in FIG. 3, causing stylet 10 to penetrate the gland 40 as indicated in FIG. 5.

As will be noted from FIG. 5, the distal end of stylet 10 includes a transverse slot 14 adjacent the sharpened end 12. When stylet 10 is inserted into gland 40, the tissue that is displaced by the stylet will project into slot 14.

Next, the physician, with his left hand, thrusts thumb tab 46 sharply forward to its stop as indicated by arrow B. As will be noted from FIG. 4, the distal end of cannula 20 has a sharpened edge 22 and has a sliding fit over stylet 10 which causes cutting edge 22 to cleanly slice through the tissue extending into slot 14 leaving a core sample 42 shown in FIG. 6.

As will now be clear, the physician has been able to hold handle 44 and guide tube 30 completely stationary with his right hand 76 during both the penetration of the gland with stylet 10 and the capturing of sample 42 by means of cutting cannula 20. Therefore, an accurate and clean core specimen is obtained. As may also be understood, the physician may carefully search the gland for the point to be investigated and once having located such point, may very quickly complete the procedure for obtaining the sample and withdraw the biopsy needle from the patient's body. The improved stability of the needle and the larger diameter of the guide effectively prevent any possibility of the stylet being inadvertently plunged further forward when the cannula is advanced, and the danger of puncturing the bladder or urethra is eliminated. Advantageously, backing out of the cannula after insertion of the stylet, as commonly occurs with prior art needles of this type, is also completely eliminated and the risk to the patient of damage and infection is greatly reduced.

Figure 7:
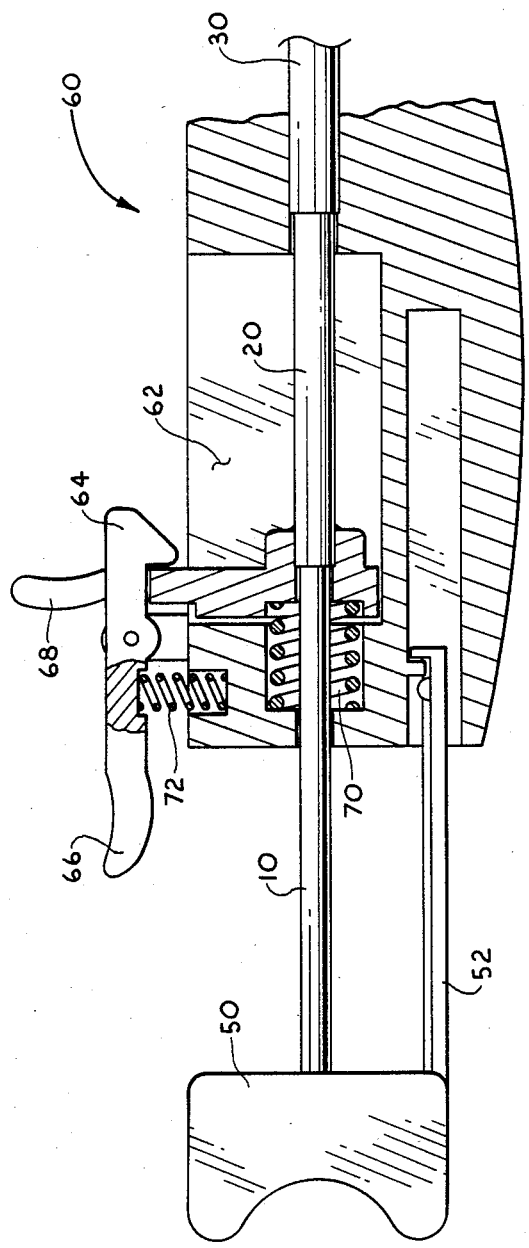
FIG. 7 illustrates a partial cross section of the handle of an alternative embodiment of my invention in which the cutting cannula is spring-loaded in its retracted position.

As discussed above, it is desirable that the advancing of the cutting cannula be performed rapidly to ensure a clean cut of the tissue sample. An alternative embodiment of my invention provides a biopsy needle which automatically ensures a clean cut of the specimen. This embodiment differs from that described above only in the handle design shown in cross-sectional view in FIG. 7. The cannula 20, when in the retracted position, is spring-loaded by means of a coil spring 70 in recess 71 at the rear portion of handle 60. Spring 70 is maintained in the compressed condition by detent lever 64 which engages thumb tab 68. A release tab 66 is provided at the rear of detent lever 64 working against coil spring 72. As will be understood, at the point at which the physician desires to move cannula 20 forward, he pushes down on release tab 66 permitting spring 77 to snap thumb tab 68 fully forward.

Although I have described my invention with respect to a transrectal biopsy needle for the prostate gland, it will be apparent to those of skill in the art that the invention may be used to obtain core tissue samples from many other parts of the human body. Similarly, although I have illustrated various lengths and diameters of elements, it is to be understood that these can be modified to suit particular applications of my invention and any such modifications are to be considered to fall within the spirit and scope of my invention.

I claim:

1. A biopsy device comprising:
   (a) a handle formed to fit an operator's head;
   (b) a set of three telescoping elements projecting from said handle in which
      (i) an outer one of said elements is a cylindrical guide tube having distal and proximal ends, said proximal end fixedly attached to said handle,
      (ii) a middle one of said elements is a cutting cannula slidably disposed within said guide tube and having a sharpened distal end thereof which in a first position is retracted into the distal end of said guide tube and which in a second position is extended a preselected distance from the distal end of said guide tube, and a proximal end within said handle said proximal end including means slidably attached to said handle,
      (iii) an inner one of said elements is a sampling stylet slidably disposed within said cannula and having a pointed distal end, a transverse sampling notch adjacent said stylet distal end, and a proximal end projecting through said handle;
   (c) a push knob attached to said proximal end of said stylet, said knob having a first position in which the pointed distal end of said stylet projects slightly beyond said distal end of said guide tube and a second position in which said pointed distal end of said stylet projects beyond said distal end of said guide tube a distance to expose said sampling notch when said cannula is in its first position; and
   (d) means associated with said handle for moving said cannula between said first position and said second position, said cannula in said second position covering said sampling notch of said stylet.

2. A transrectal biopsy device for obtaining core samples of prostatic tissue comprising:
   an elongate handle formed to fit the palm of a human hand and having a longitudinal opening therethrough;
   a cylindrical hollow fixed guide tube inserted in said longitudinal opening and attached to a forward end of said handle; said guide tube extending forwardly therefrom;
   a hollow cannula disposed in a telescoping arrangement within said guide tube, said cannula having a cutting distal end thereof and having means slidably attached to said handle for retracting said distal end of said cannula so as to be within said guide tube and for moving said cutting distal end thereof to a position extending from the distal end of said guide tube;
   a sampling stylet having a sharpened distal end and a transverse sampling notch therein adjacent said distal end, said stylet disposed in a telescoping arrangement within said cannula and having a proximal end extending from said longitudinal opening at a rear end of said handle and said distal end extending slightly from said distal end of said guide tube;
   a push knob attached to said proximal end of said stylet, said push knob having a rearward position in which the distal end of said stylet projects slightly from the distal end of said fixed guide tube in which said sampling notch is within said guide tube and said cannula, when said cannula is retracted and a forward position in which the distal end of said stylet projects a second distance from said distal end of said guide tube thereby exposing said sample notch and in which said cannula when in its extended position covers said sampling notch; and
   said handle and said guide tube thereby permitting and operator to hold said handle in one hand and to contact the distal end of said guide tube with the index finger of that hand and thereby guide the distal ends of said stylet and said cannula to a selected point on a prostate gland transrectally.

3. A device for collection of a sample from human tissue for biopsy purposes comprising:
- a handle formed to be held in the human hand and having a forward end and a rearward end;
- a hollow guide tube having a proximal end attached to said handle and a distal end projecting a preselected distance from said forward end of said handle, said guide tube fixed to and stationary with respect to said handle;
- a cannula telescopically disposed within said guide tube and having a proximal end within said handle and a distal end adjacent the distal end of said guide tube, said distal end sharpened to provide a cutting edge thereof;
- cannula moving means disposed in said handle and attached to the proximal end of said cannula, said cannula moving means including means slidably attached to said handle for moving said cannula from a retracted first position in which said cutting edge thereof is within said guide tube to an extended second position in which said cutting edge projects a preselected distance from said distal end of said guide tube;
- a stylet telescopically disposed within said cannula and having a proximal end extending through said rearward end of said handle and a distal end sharpened to a point, said stylet having a tissue-collecting notch adjacent said distal end thereof; and
- a push knob attached to said proximal end of said stylet for moving said stylet from a retracted first position in which said point projects slightly from the distal end of said guide tube to an extended second position in which said point projects a preselected distance from said distal end of said guide tube; and
- said push knob is adapted to move said stylet from its retracted first position to its extended second position when said cannula is in said first position and when said distal end of said stylet is in contact with tissue to be sampled to thereby cause tissue to project into said notch, and said cannula moving means is adapted to thereafter move said cannula to its extended second position thereby cutting a core sample of the tissue extending into said notch.

4. The device as defined in claim 3 in which said handle includes a convexly curved portion adapted to fit the palm of the hand.

5. The device as defined in claim 3 which further comprises:
- first stop means for defining said retracted position and said extended position of said cannula; and
- second stop means for defining said retracted position and said extended position of said stylet.

6. The device as defined in claim 5 in which said second stop means includes a stopbar attached to said push knob and having a first stop limiting the movement of said stylet in the retracted direction and a second stop limiting the movement of said stylet in the extended direction.

7. The device as defined in claim 5 in which:
- said handle includes an aperture therein; and
- in which said cannula moving means includes a thumb tab slidably disposed in said aperture, the proximal end of said cannula attached to said thumb tab, said aperture serving as said first stop means.

8. The device as defined in claim 7 which further comprises:
- bias means for urging said thumb tab and said cannula in the extended direction;
- detent means for holding said thumb tab and said cannula in the retracted position; and
- release means for releasing said detent to permit said cannula to sharply extend.

9. A method of obtaining a tissue sample from a prostate gland utilizing a biopsy device having a guide tube attached to a handle, an extendable cannula telescopically disposed in the guide tube and having a sharpened distal end thereof and a thumb tab at its proximal end for extending the cannula, and an extendable sampling stylet telescopically disposed in the cannula having a sharpened distal end, a sampling notch adjacent the distal end, and a knob at its proximal end for extending the stylet, comprising the steps of:
- placing the handle of the biopsy device in the palm of one hand with the distal end of the guide tube held in contact with the tip of the index finger of that hand;
- inserting the index finger and the guide tube transrectally to contact the rectal wall adjacent the prostate gland of the patient;
- locating a desired area of the gland with the tip of the finger and holding the distal end of the guide tube at a desired point in the area;
- holding the handle and guide tube steady with the hand;
- moving the stylet knob in the extending direction using the other hand so as to cause the sharpened distal end of the stylet to penetrate the gland at the desired point and to cause tissue of the gland to project into the notch;
- slicing a core of tissue in the stylet sampling notch by moving the cannula by means of the thumb tab in the extending direction into the tissue of the gland using the other hand; and
- withdrawing the index finger, the guide tube, the stylet and the cannula from the gland and the rectum.

* * * * *